US008029431B2

(12) United States Patent
Tononi

(10) Patent No.: US 8,029,431 B2
(45) Date of Patent: Oct. 4, 2011

(54) METHOD AND APPARATUS FOR PROMOTING RESTORATIVE SLEEP

(75) Inventor: Giulio Tononi, Verona, WI (US)

(73) Assignee: Wisconsin Alumni

( * ) Notice: Subject to any disclaimer, the term of this patent is extended or adjusted under 35 U.S.C. 154(b) by 1013 days.

(21) Appl. No.: 11/863,047

(22) Filed: Sep. 27, 2007

(65) Prior Publication Data

US 2008/0081941 A1 Apr. 3, 2008

Related U.S. Application Data

(60) Provisional application No. 60/827,335, filed on Sep. 28, 2006.

(51) Int. Cl.
*A61N 1/00* (2006.01)
(52) U.S. Cl. .......................................................... 600/9
(58) Field of Classification Search ................ 600/9–15, 600/393, 544, 26–28; 607/72–76, 45
See application file for complete search history.

(56) References Cited

U.S. PATENT DOCUMENTS

| 5,335,657 A | 8/1994 | Terry, Jr. et al. |
| 2004/0215236 A1 | 10/2004 | Lattner et al. |
| 2005/0177192 A1 | 8/2005 | Rezai et al. |
| 2006/0003985 A1 | 1/2006 | Renger et al. |
| 2006/0205993 A1 | 9/2006 | Fischell et al. |
| 2006/0212091 A1 | 9/2006 | Lozano et al. |

OTHER PUBLICATIONS

PCT International Search Report for PCT Application No. US07/79747, dated Jan. 29, 2008, ISA/US.
Massimini, et al., Breakdown of Cortical Effective Connectivity During Sleep, Science, Sep. 30, 2005, pp. 2228-2232, vol. 309, American Association for the Advancement of Science (AAAS), Washington, DC, USA.
Esser, et al., A Direct Demonstration of Cortical LTP in Humans: A Combined TMS/EEG Study, Brain Research Bulletin, vol. 69 (2006) pp. 86-94, Elsevier, Amsterdam, Netherlands.
Huber, et al., Local Sleep and Learning, Nature, Vo. 430, Jul. 1, 2004, pp. 78-81, Nature Publishing Group, New York, New York, USA.
Tonini, et al., Sleep and Synaptic Homeostatis: A Hypothesis, Brain Research Bulletin, vol. 62 (2003) pp. 143-150, Elsevier, Amsterdam, Netherlands.
Fontanini, et al., Slow-waves in the Olfactory System: An Olfactory Perspective on Cortical Rythms, Trends in Neurosciences, vol. 29, Issue 8, Aug. 2006, pp. 429-437, Cell Press (a division of Elsevier), Amsterdam, Netherlands.
Tonini, et al., Sleep Function and Synaptic Homeostatis, Sleep Medicine Reviews, vol. 10 (2006) pp. 49-62, Elsevier, Amsterdam, Netherlands.
Lins, Stephanie, Supplementary European Search Report for EP App. No. EP 07 84 374, Aug. 13, 2010, European Patent Office, Munich, Germany.

*Primary Examiner* — John Lacyk
(74) *Attorney, Agent, or Firm* — Boyle Fredrickson, S.C.

(57) ABSTRACT

Brain stimulation is used to promote or induce slow-wave activity thought to be associated with the restorative properties of sleep. In a preferred embodiment, transcranial magnetic stimulation is used to provide neural stimulation at a frequency approximating natural slow-wave activity.

22 Claims, 6 Drawing Sheets

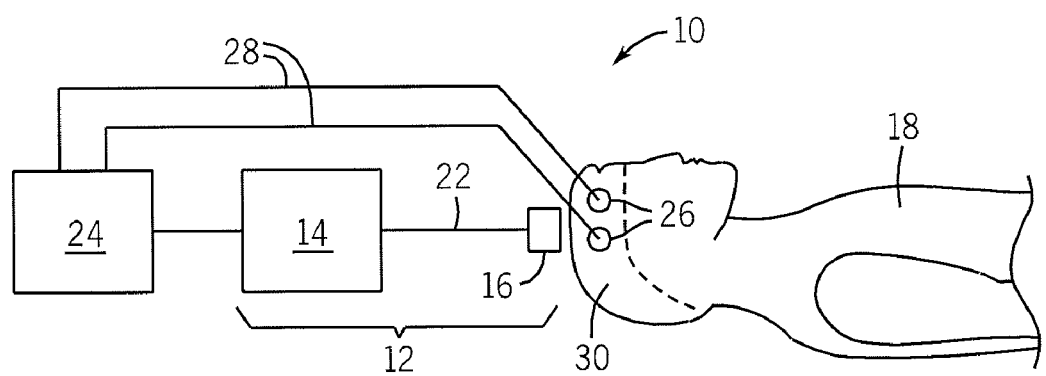
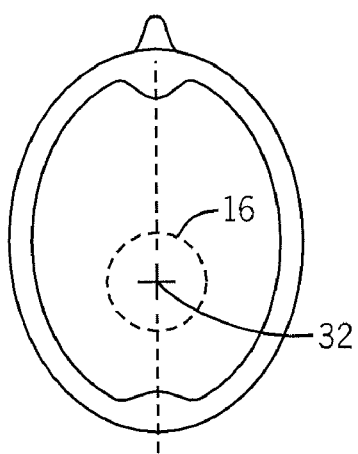
FIG. 2
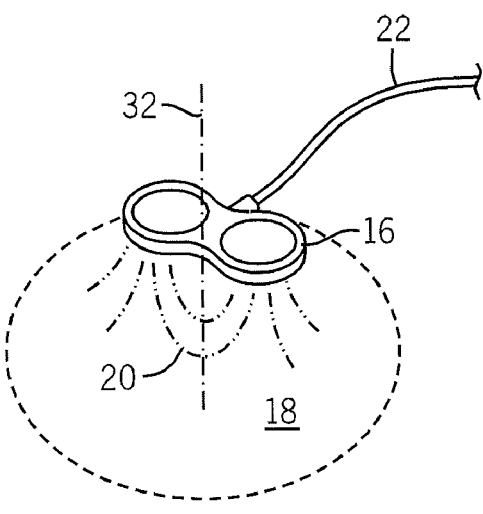
FIG. 3
FIG. 1

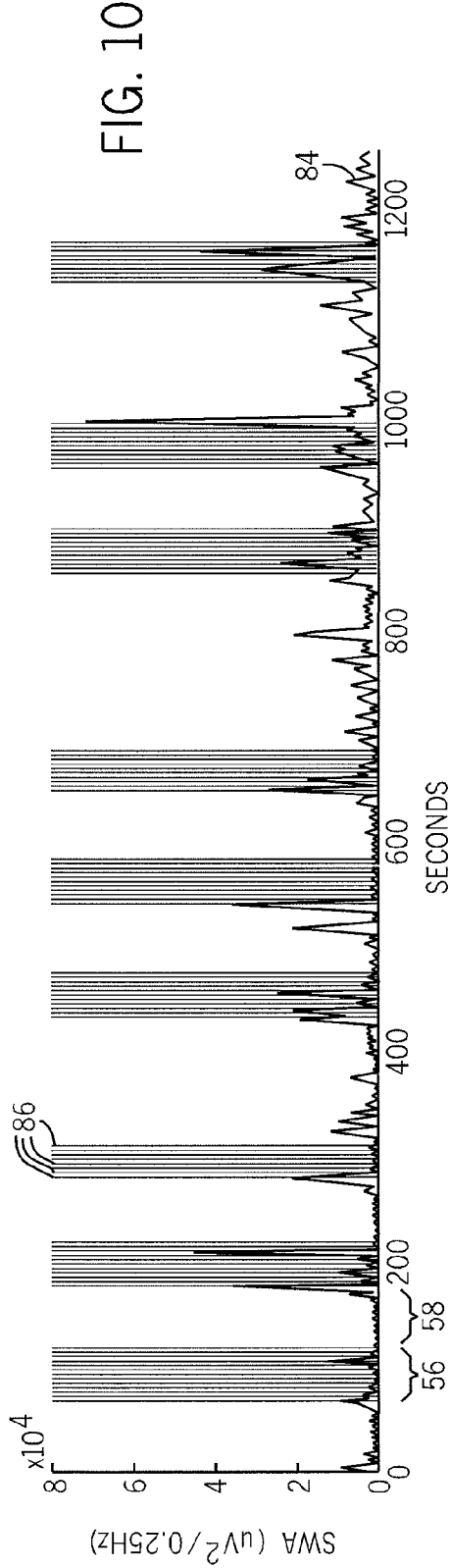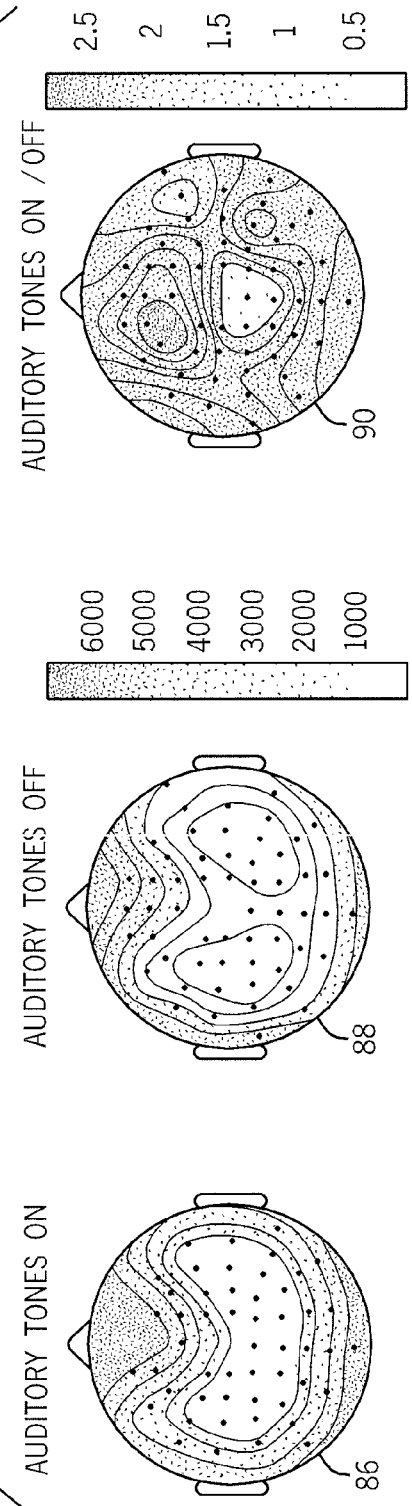
FIG. 10
FIG. 11

METHOD AND APPARATUS FOR PROMOTING RESTORATIVE SLEEP

CROSS-REFERENCE TO RELATED APPLICATIONS

This application claims the benefit of U.S. provisional application 60/827,335 filed Sep. 28, 2006 hereby incorporated by reference.

STATEMENT REGARDING FEDERALLY SPONSORED RESEARCH OR DEVELOPMENT

This invention was made with United States government support awarded by the following agency: DOD ARPA DAAD 19-02-1-0036. The United States government has certain rights in this invention.

BACKGROUND OF THE INVENTION

The present invention relates to devices for promoting or inducing restorative sleep and, in particular, to a non-pharmacological method of promoting slow-wave activity in the brain thought to be essential for restful sleep.

The importance of regular, adequate restful sleep is well recognized, however, many people find it difficult to obtain the amount or quality of sleep they require. Generally, techniques for promoting restful sleep do not increase the efficiency of sleep, but still require an individual to obtain approximately eight hours of sleep for every 24 hours.

Conventional sleeping pills can facilitate the induction of a sleep-like state, but are generally ineffective in promoting the restful stages of sleep thought to be necessary to provide the full benefits of sleeping. Sleeping pills of all kinds have the disadvantage of being difficult to counteract if the person taking the sleeping pill needs to be roused unexpectedly, for example, when used by first responders, physicians who are on-call, or military personnel.

Stimulants, such as caffeine, may postpone the need for sleep, but increase a sleep deficit which must ultimately be repaid.

SUMMARY OF THE INVENTION

The present invention provides a method of inducing or promoting slow-wave activity (SWA) in the brain of a resting person thought to be associated with the restorative aspects of sleep by using an external repeated stimulus that promotes slow-wave activity. Slow wave activity, as used herein, includes slow waves and related phenomenon such as "sleep spindles". It is believed the invention may promote restful sleep for those who have trouble sleeping and/or shorten the amount of sleep needed by others. The stimulus may be applied at a time when the brain is susceptible to slow-wave sleep and may be turned off at any time, allowing the person to wake up on demand without grogginess beyond naturally occurring sleep "inertia".

Specifically then, the present invention provides an apparatus for promoting restorative sleep that provides a brain stimulator for periodic stimulation of brain at a frequency substantially less than five Hz to promote slow wave activity.

It is thus an object of at least one embodiment of the invention to provide a non-pharmacological sleeping aid that may promote or induce the most restful kind of sleep.

The invention may further include a sleep monitor monitoring a resting person to detect brain activity and the brain stimulator is controlled by the sleep monitor.

Thus, it is an object of at least one embodiment of the invention to coordinate the brain stimulation with natural brain activity, either sleep stages or possibly phasing of slow wave activity, to improve the effect of the brain stimulation.

The sleep monitor may activate the brain stimulator at the onset of a predetermined amount of slow-wave activity.

Thus, it is an object of at least one embodiment of the invention to provide a simple method of detecting an effective time to apply the brain stimulation.

The brain stimulator may be a transcranial magnetic stimulation device.

It is an object of at least one embodiment of the invention to provide a non-invasive means of stimulating the brain that may directly promote restful sleep.

The frequency of transcranial magnetic stimulation may be less than five Hz.

It is an object of at least one embodiment of the invention to permit the use of low powered transcranial magnetic stimulation facilitating a portable TMS-type device.

The sleep monitor may be an EEG device providing electrodes positioned on a resting person.

It is thus an object of at least one embodiment of the invention to provide both an accurate way of timing the stimulation and further to allow logging of EEG signals that may quantify the effectiveness of the treatment.

The apparatus may provide a helmet or similar device holding the stimulation coils of the transcranial magnetic stimulation device and EEG electrodes positioned on the resting person's head.

It is thus another object of at least one embodiment of the invention to provide a simple and comfortable apparatus that may correctly position a TMS device and hold sensors used to monitor brain function.

The apparatus may further include a scheduling unit for de-activating the brain stimulator after a pre-determined interval, for a predetermined interval, so that the sleep monitor may later reactivate the brain slow wave stimulator at a renewed onset of the sleep level.

Thus, it is an object of at least one embodiment of the invention to provide an apparatus that may mimic or enhance the natural patterns of deep and light sleep experienced by normal sleepers.

The brain stimulator may in one embodiment be audio signals such as short tones.

Thus, it is another object of at least one embodiment of the invention to provide an extremely simple and low cost system for promoting restful sleep.

The brain stimulator may in one embodiment be a nasal appliance periodically stimulating the olfactory nerves. In another embodiment, the neuron stimulator may use electrodes applied directly to the skin of the resting person's head to induce electrical current therebetween.

Thus, it is another object of at least one embodiment of the invention to provide a system that may flexibly be used with other forms of neural stimulation.

The transcranial magnetic stimulation may be applied to the resting person's sensory-motor/parietal cortex near a midline of the brain.

It is another object of at least one embodiment of the invention to provide stimulation at a location empirically determined to provide for increased slow-wave activity.

These particular objects and advantages may apply to only some embodiments falling within the claims and thus do not define the scope of the invention.

BRIEF DESCRIPTION OF THE DRAWINGS

FIG. 1 is a simplified block diagram of a preferred embodiment of the present invention using a TMS stimulator and showing a TMS coil positioned on top of the resting person's head and a control unit receiving EEG signals to identify an appropriate timing of the TMS stimulation;

FIG. 2 is a cross section through the head of the patient in FIG. 1 in a transverse plane showing a preferred location of the TMS stimulation;

FIG. 3 is a perspective view of a butterfly TMS coil showing lines of flux that may penetrate into the brain of the resting patient;

FIG. 10 is plot showing slow wave activity occurring during the application of periodic audio tones;

FIG. 11 is a set of three planar maps of the brain showing the strength of slow-wave activity without the audio tones, with the audio tones and the difference between the two;

DETAILED DESCRIPTION OF THE PREFERRED EMBODIMENT

Figure 4:
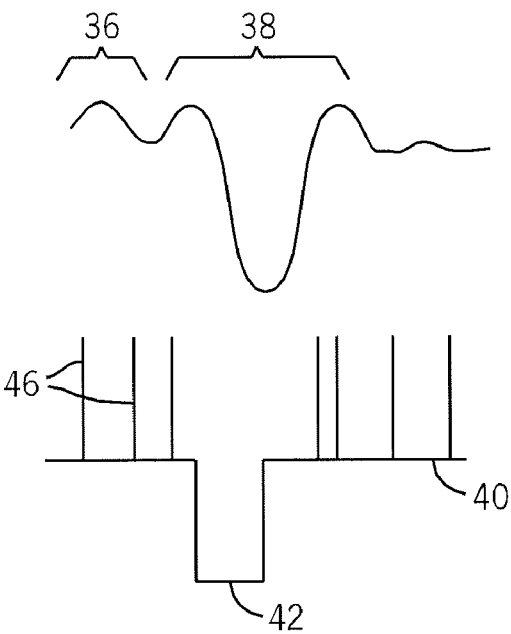
FIG. 4 is a simplified EEG waveform of a slow-wave and a model of an individual neuron firing that in combination with other neurons produces the slow wave.

Referring now to FIG. 1, a first embodiment of the apparatus 10 of the present invention may use a transcranial magnetic stimulation (TMS) device 12 having a power unit 14 and a coil 16. During operation, a set of capacitors or other energy storage devices in the power unit 14 are charged and then rapidly connected to the coil 16 by leads 22 creating a monophasic or biphasic pulse of current in the coil 16 positioned at the top of the head of a resting patient 18.

Referring now to FIG. 1, the pulse of current causes a rapidly changing magnetic flux 20 in the brain of the patient 18. This changing magnetic field, in turn, induces current within the brain tissue that stimulates neuron activity. The coil 16 may, as depicted in FIG. 3, may be a "butterfly coil", having windings in a figure-eight pattern to provide opposed magnetic flux in adjacent loops focusing the flux 20 to a compact region. Other coils such as single loop coils and the like may also be used.

TMS devices 12 are commercially available, for example, from Magstim of Whitland, South West Wales, United Kingdom.

Referring again to FIG. 1, the TMS device 12 is in turn controlled by a controller 24, the latter receiving EEG signals from electrodes 26 placed, for example, on the patient's scalp. As few as two electrodes may be used, however, multiple electrodes may also be contemplated.

The controller 24 thus includes standard EEG processing circuitry including amplifiers, gating circuitry and filters to provide for continuous EEG signals without disruption by the pulse produced by the TMS device 12 although this feature is not required in the present invention. EEG circuitry suitable for use with the present invention may be obtained from Nexstim of Helsinki, Finland under the trade name Eximia. The Nexstim device provides for a sample and hold amplifier that is specifically developed for use in monitoring EEG during TMS stimulation.

The EEG signal may be digitized for automatic computer analysis of slow-wave activity, in the time or frequency domain, as will be understood in the art, and for recording in a logging operation to be described. In this way, the EEG of the resting patient 18 may be monitored and used to control the TMS device 12 as will be described.

The electrode leads 28 connecting the controller 24 to the EEG electrodes 26 and/or portions of the electrodes 26 themselves, and the coil 16 of the TMS device 12 may be fitted to a cap 30 used to retain them in position on the head of the resting patient 18. The cap 30 may also provide for noise masking earplugs or earphones (not shown).

Referring now to FIG. 2, in the currently preferred embodiment, the coil 16 is positioned so that its central axis 32 (generally extending along a center of the projection of flux from the coil into the head) enters the top (superior side) of the head of the resting patient 18 at the sensory-motor/parietal cortex near a midline of the brain. Pre-frontal areas are avoided because they promote excessive blinking, however new coil designs or methods may allow these areas to be used as well. It is expected that the ideal location will vary by individual and may be determined, as will be described below, by monitoring the effect of the pulses produced by the TMS device 12 on increasing the power in the slow-wave bandwidth the EEG signals over a short or long term.

Referring now to FIG. 4, the EEG signal 34 received by the controller 24 may generally show background neural activity 36 punctuated by one or more slow-waves 38. The slow-waves are characterized by a frequency content centered in a range from 0.5 to 5.0 Hz. Studies of the electrical potentials of individual neurons 40 suggest that short periods of hyperpolarization/depolarization 42 of individual neurons occurring in rough synchrony produce the slow-wave 38 detected by the EEG signal. Under the hypothesis of synaptic homeostasis, these periods of hyperpolarization/depolarization 42 cause a downscaling of the synaptic weights of the neurons of the brain. See, generally, Tononi, Giulio, Cirelli, Chiara, "Sleep Function and Synaptic Homeostasis," *Sleep Medicine Reviews*, 2006, 10, 49-62.

During wakefulness, synapses on average tend to become stronger by virtue of learning. This makes learning possible, but it comes at a price of increased energy consumption, space demands, and need for biochemical supplies for neurons and synapses. During sleep, the hyperpolarization/depolarization of neurons in the brain produce a global weakening of connections. This global weakening of connections downscales the synaptic strength between the pre-synaptic and post-synaptic neurons for many neurons proportionally to the existing strength.

A weakening of all neural connections by a roughly equal percentage tends to prune weaker synaptic connections thereby reducing saturation of the neural structure. The downscaling further lowers the energy costs of strongly connected neurons and reduces the space costs of multiple neuron connections while providing a general increase in the signal to noise ratio of neural signals.

To the extent that neural downscaling is a principal element of restorative sleep, and slow-waves 38 represent the mechanism of neural downscaling, the promotion of the slow-waves 38 may improve the efficiency of restorative sleep.

Figure 5:
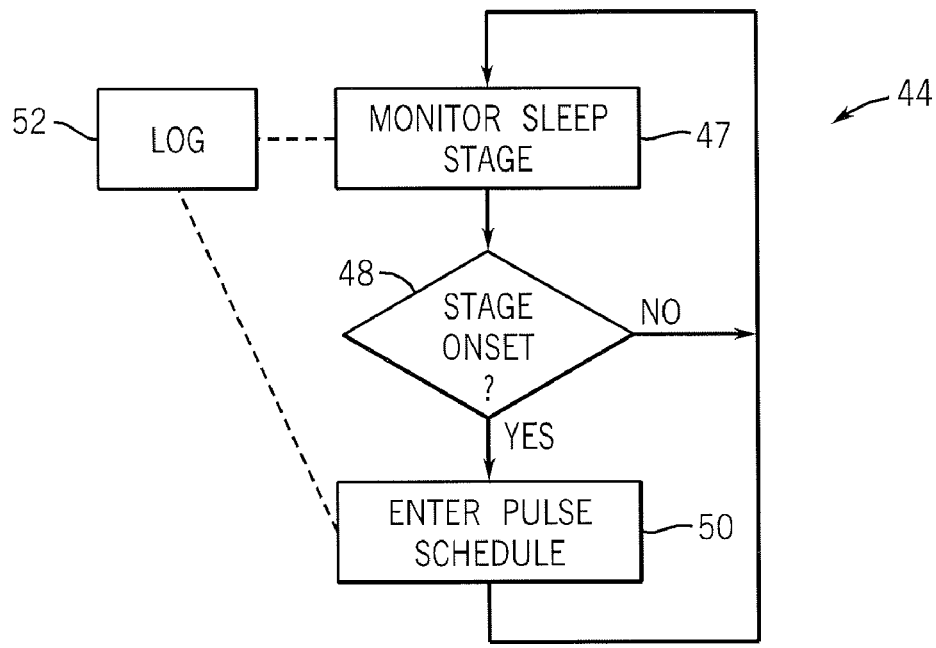
FIG. 5 is a flowchart of a program executed by the controller of FIG. 1 to control the TMS stimulator.

Referring now to FIG. 5, the controller 24 in a principle embodiment of the present invention executes a stored program 44 that executes a process block 47 monitoring, through the EEG electrodes 26, the progression of the resting patient 18 through various stages of sleep. In particular, the controller 24 monitors four non-REM (rapid eye movement) sleep stages that accompany the progression from light to deep sleep and may be summarized as follows:

Stage 1 is a transitional period of very light sleep in which chemical changes occur, such as permit the generation of slow-wave activity (SWA). Approximately, five percent of non-REM sleep is spent in stage 1.

Stage 2 is the beginning of slow-wave activity. Approximately, 45 percent of non-REM sleep is spent in Stage 2. This stage is characterized by waveforms called sleep spindles and K-complexes, the latter thought to be essentially identical to the largest slow-waves seen in later stages. Sleep spindles are waves having frequency content between approximately 12 to 15 Hz and, as described, the K-complex or slow-waves are waves having frequency content between approximately 0.5 and 5.0 Hz.

Stage 3 is entered as sleep advances and becomes deeper and exhibits an increase in slow-wave activity.

Finally, Stage 4 is characterized by very deep sleep. Roughly, thirteen percent of non-REM sleep is spent in this stage. During stages 3 and 4, K-complexes are replaced by slow-waves or oscillations that unlike K-complex-like responses are not induced by peripheral stimuli but occur spontaneously up to 1-2 times per second.

Referring again to FIG. 5, at process block 47, the program 44 may deduce the resting person's stage of sleep by measuring the power spectrum of the EEG signals concentrated in the bandwidth of 0.5 to 4.0 Hz corresponding to slow-waves 38 and comparing that power to one or more empirically determined thresholds.

Generally, before stage 2, it is believed that the brain is not susceptible to induced SWA because of a lack of antecedent chemical preparation of the brain. Accordingly, at decision block 48 the occurrence of a predetermined threshold stage, preferably stage 2 or later, is detected. Only if the desired threshold stage has been reached, does the program proceed to process block 50 where a TMS schedule is entered. Otherwise, the program loops back to the monitoring of process block 47.

When the desired threshold stage has been reached, a predetermined TMS schedule of process block 50 is used to provide for a periodic pulsing of the TMS device delivering, in the preferred embodiment, periodic pulses at a frequency of 0.5 to 1.0 Hz or generally at a frequency less than the 5.0 Hz upper limit of the bandwidth of the slow-waves 38 and a frequency at which undesirable effects of the stimulation may occur.

Figure 6:
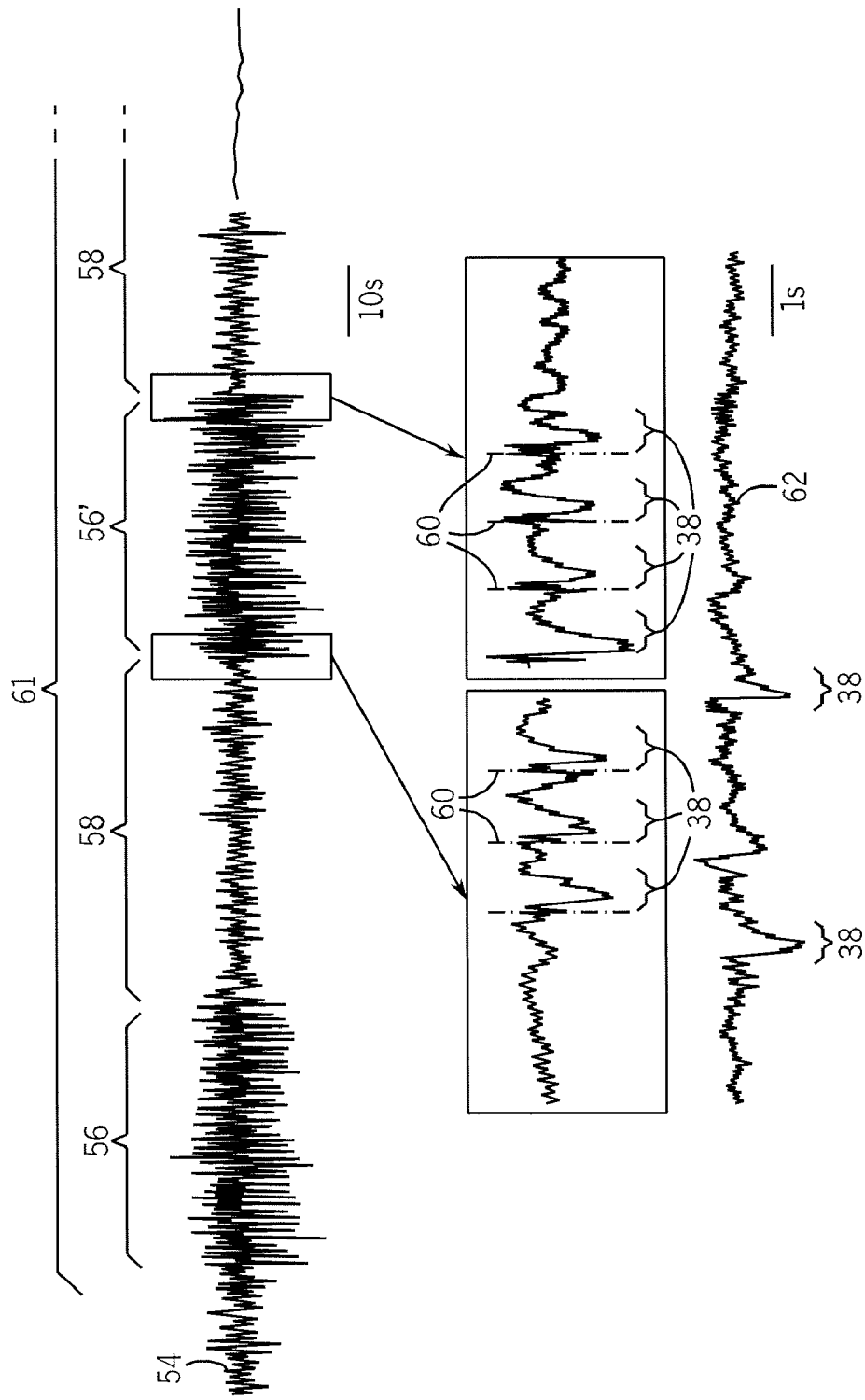
FIG. 6 is a set of plots showing an EEG signal during periods of TMS excitation per the present invention showing an increase in slow-wave activity, FIG. 6 further showing expanded portions of the EEG signal indicating the timing of the TMS pulses and the resulting slow-waves positioned above a spontaneous EEG signal.

Referring now to FIGS. 5 and 6, following the pulse schedule in the controller 24, the TMS may be applied during TMS application intervals 56 and 56', each followed optionally by rest intervals 58, and this cycle repeated for a stage duration 61 all of which may be empirically determined. During the TMS application intervals 56, 56', TMS pulses 60 may be applied such as produce subsequent slow-waves 38 resulting either from increased participation in the slow-wave activity among brain or improved synchronization. This promoted slow-wave activity may be contrasted to spontaneous slow-wave activity of lesser magnitude and frequency of EEG trace 62. Preliminary results indicate that power in the bandwidth of the slow-waves 38 may be increased by 80 percent to 500 percent not only near the stimulation site but also throughout the scalp.

When the stage duration 61 has expired, the stimulation is stopped and the program returns to the monitoring and detection of stages at process blocks 47 and decision block 48 until transition out of the threshold stage (detected at decision block 48) to a lower stage occurs. The stimulation remains dormant until there is a transition into the threshold stage from a lower stage at which time the above process may be repeated.

In this way, the patient is allowed to move naturally up and down through the sleep stages with sleep cycles 2, 3 and/or 4 being augmented with the TMS device to promote a larger amount of slow-wave activity. In an alternative embodiment, it may be possible to apply the stimulation continuously.

In an alternative embodiment, the TMS stimulation may begin in stages 1 or 2 so as not simply to enhance sleep depth but to facilitate its induction converting stage 1 or 2 sleep into deep stage 4 sleep. In this way, total sleep time may possibly be decreased to create a "power nap". In an alternative embodiment the TMS stimulation may begin even during wakefulness to promote the induction of sleep.

Referring again to FIG. 5, during the process blocks 47-50, the EEG signals 54 may be logged as indicated by process block 52 to measure the effectiveness of the TMS stimulation. The logging records the EEG signal 54 and may also extract power spectra from the slow-wave bandwidth to provide statistics for the total slow-wave activity produced during the treatment session that may be used to improve the treatment parameters. The logging of process block 52 may also be used in a test mode in which TMS stimulation is produced and power spectra analyzed to determine the appropriate location for the coil 16 for a given individual.

Figure 7:
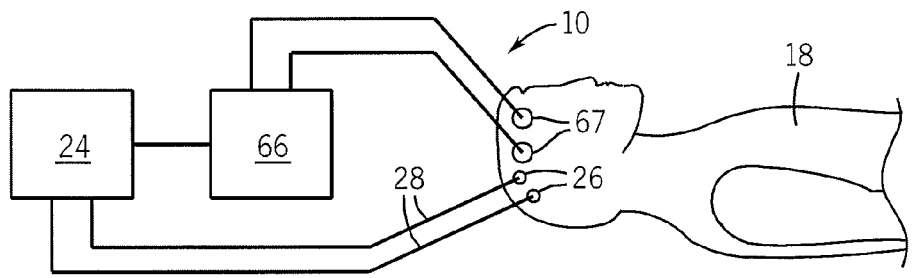
FIG. 7 is a figure similar to that of FIG. 1, showing an alternative embodiment which may use DC stimulation instead of the TMS stimulation.

Referring now to FIG. 7, in an alternative embodiment, it is possible that the TMS device 12 may be replaced with a DC power source 66 that provides a DC current across electrodes 67, such as may provide some stimulation to brain. In this approach, the TMS pulses are replaced by short DC pulses or AC pulses conducted through the skin and presumably into neural tissue to provide similar stimulation of the neurons. In all other respects, the device of FIG. 7 would operate in a manner analogous to that described above.

Figure 8A:
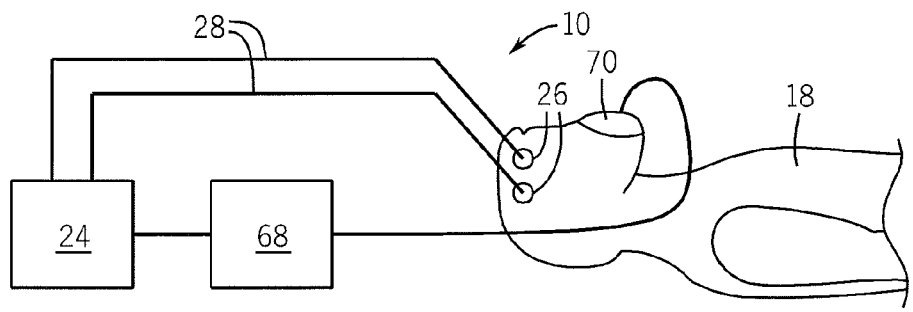
FIGS. 8a and 8b are figures similar to that of FIGS. 1 and 7 showing a system using olfactory stimulation and vestibular stimulation respectively.
Figure 8B:
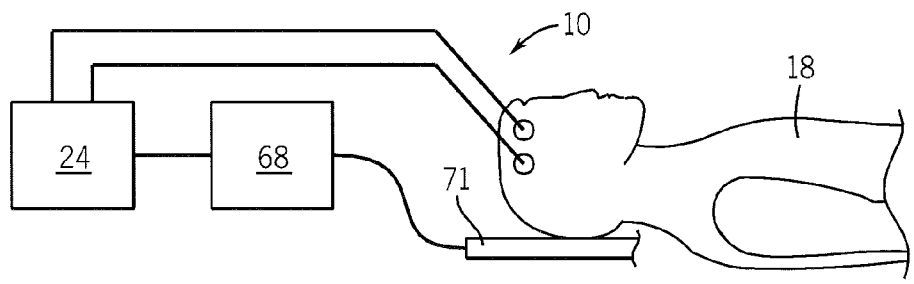

Alternatively, as shown in FIG. 8a, the TMS device 12 may possibly be replaced by an olfactory stimulator 68 providing stimulation of brain through the pathway of the olfactory nerves or tactile nerves of the nose using air jets directed on a periodic basis through mask 70 to the patient's nostrils. The stimulation of the olfactory nerves may be superior to audio or optic stimulation because the olfactory nerves are not relayed by the thalamus, which may block stimulation during the sleep cycle. Similarly, as shown in FIG. 8b, the body's vestibular nervous system may be used for a stimulation path with a gently accelerating sleep platform 71 providing a 0.4 to 5.0 hertz periodicity. The sleep platform 71 may use electromagnetic actuators driven at the desired frequency according to techniques well known in the art. As before, the stimulation may be continuous or timed to particular sleep stages.

Figure 9:
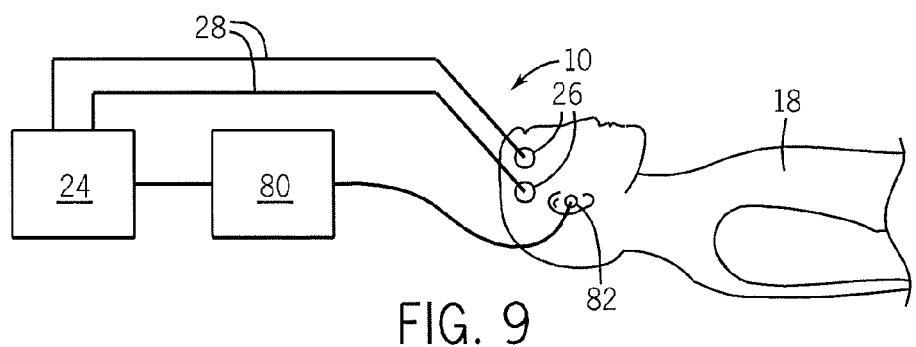
FIG. 9 is a figure similar to that of FIGS. 7 and 8 showing an alternative embodiment using audio tones instead of TMS or olfactory stimulation.

Referring now to FIG. 9, in an alternative embodiment, the controller 24 may trigger an audio tone generator 80, producing, for example, short one kilohertz tones of approximately ¼ second, t a frequency of 0.4-5.0 hertz. The audio tone generator 80 may provide the audio signal through ear buds 82 fit into the patient's ear canal or headphones or the like attached to a cap as described above. The audio tones may be repeated for a number of application intervals 56 separated by rest intervals 58 and may be keyed to sleep stages or EEG data as described above.

Referring now also to FIG. 10, a plot providing power in the slow wave frequency band strongly suggests that there is an increase in slow wave activity during the audio stimulations 86, each indicated by a vertical line. The stimulation pattern as shown, as has been varied slightly with the intent of gathering varied experimental data.

As shown in FIG. 11, slow wave activity in the brain (darker shades indicating more slow wave activity) occurs both when the audio tones are "on" per map 87 and when the audio tones are "off" per map 88, but such slow wave activity is substantially increased when the audio tones are on, as shown by brain map 90 indicating the difference between brain maps 87 and 88. At present, the audio tones appears to increase slow wave activity but the resulting slow wave activity does not exhibit the tight phase relationship with the brain stimulation that is obtained with TMS stimulation.

Figure 12:
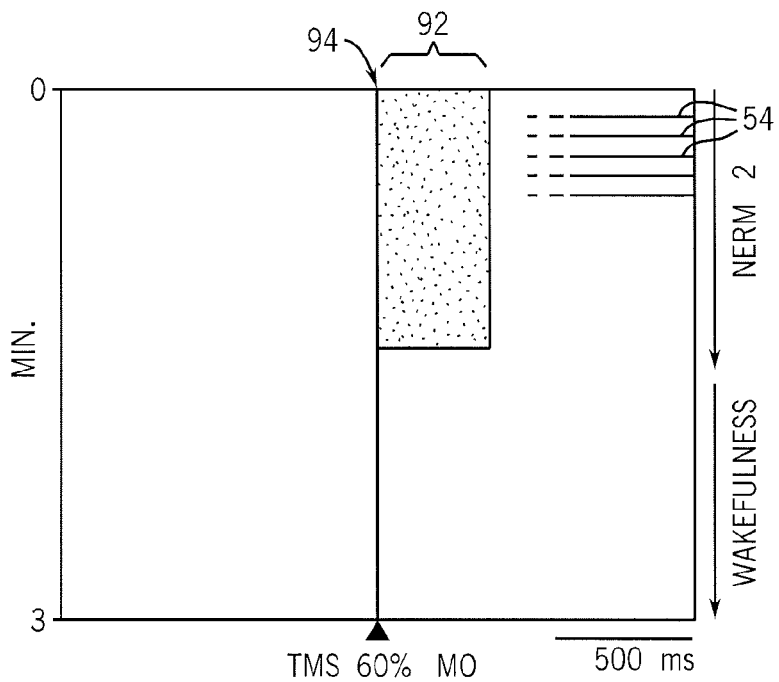
FIG. 12 is a rasterized time plot of brainwave activity in the frequency band of slow waves where shading indicates signal amplitude, showing slow waves evoked after TMS stimulation for non-REM stage 2 sleep but not evoked for a period of wakefulness.
Figure 13:
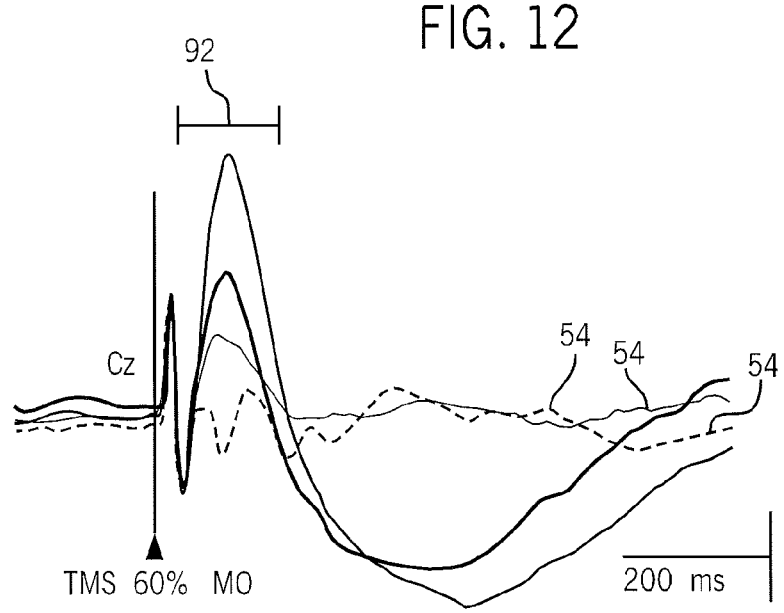
FIG. 13 is a plot of multiple EEG signals for different sleep stages aligned to a period of TMS stimulation showing different amplitudes of evoked slow waves as a function of sleep stage.

Referring now to FIGS. 12 and 13, during a periods 92 of the EEG signals 54 (following TMS stimulations occurring at times 94) significant slow wave activity occurs, linked to the timing of the TMS stimulations and manifest by the initial upward rising peak of the slow wave at periods 92. As is evident both from FIGS. 11 and 12, this evoked response occurs only during non-REM sleep and not during wakefulness.

Referring to FIG. 12, the amount of evoked slow wave activity increases as one progresses from non-REM sleep stage one through non-REM sleep stages 3-4 and is extremely low or nonexistent in wakefulness.

This close phase or time relationship between the TMS stimulation and an amplitude of a resulting slow wave, raises the possibility that the present invention may also be used to detect and quantify a state of consciousness of a person. In this respect, the invention may have application in the field of anesthesiology. In such an application, a healthcare worker may employ the invention described with respect to FIG. 1, for example, in the surgical suite with controller 24 analyzing brain waves after each stimulation by the TMS device 12 to assess the state of consciousness of the individual. Such a device may use the controller 24 to assess power in the slow wave frequency range immediately after the TMS stimulus for a predetermined window of time, for example, one-half second, and use the power or amplitude of the slow wave in that window to provide a quantitative measurement of consciousness state.

Additional analysis and disclosure is contained in the article "Triggering sleep slow waves by transcranial magnetic stimulation" PNAS, May 15, 2007, vol. 104, no. 20, 8496-8501, hereby incorporated by reference.

It is specifically intended that the present invention not be limited to the embodiments and illustrations contained herein, but include modified forms of those embodiments including portions of the embodiments and combinations of elements of different embodiments as come within the scope of the following claims.

I claim:

1. An apparatus for promoting restorative sleep comprising:

a brain stimulator for non-invasive stimulation of the brain at a frequency substantially less than 5 Hz to promote slow wave activity; and a sleep monitor controlling the brain stimulator and monitoring the brain to detect an amount of slow-wave activity in the brain indicating non-REM sleep, wherein the sleep monitor activates the brain stimulator at an onset of a predetermined amount of slow-wave activity indicating non-REM sleep.

2. The apparatus of claim 1 wherein the brain stimulator is selected from the group consisting of audio stimulation and vestibular stimulation.

3. The apparatus of claim 1 wherein the brain stimulator is a transcranial magnetic stimulation device.

4. The apparatus of claim 3 including a positioner positioning a coil of the transcranial magnetic stimulation device at the resting person's sensory-motor/parietal cortex near the midline of the brain.

5. The apparatus of claim 3 wherein the transcranial magnetic stimulation device stimulates brain at a frequency less than 1 Hz.

6. The apparatus of claim 1 wherein the sleep monitor is an EEG device providing electrodes positioned on the resting person to detect a predetermined level of sleep/wake activity.

7. The apparatus of claim 6 further including an electronic data log recording the EEG and indicating times of periodic stimulation of the brain by the brain stimulator.

8. The apparatus of claim 7 wherein the electronic data log provides a measurement of power at less than 5 Hz.

9. The apparatus of claim 1 further including a head appliance holding a stimulation coil of a transcranial magnetic stimulation device and EEG electrodes positioned on the resting person's head.

10. The apparatus of claim 1 further including a sequencing unit for deactivating the brain stimulator after a predetermined interval; wherein the sleep monitor may later reactivate the brain stimulator at a renewed onset of the sleep level.

11. The apparatus of claim 1 further including a sequencing unit for deactivating the brain stimulator after a predetermined interval.

12. The apparatus of claim 1 wherein the brain stimulator is an audio generator delivering an audio pulse.

13. The apparatus of claim 1 wherein the brain stimulator is a nasal appliance periodically stimulating the nose.

14. The apparatus of claim 13 wherein the nasal appliance provides periodic bursts of air.

15. The apparatus of claim 1 where the brain stimulator provides at least two electrodes at least one of which is applied to skin of the resting person's head to induce an electrical current therebetween.

16. A method of promoting restorative sleep comprising the steps of applying a transcranial magnetic stimulation to a resting person at a frequency less than 5 Hz to promote EEG slow-wave activity in a brain of the resting person.

17. The method of claim 16 further including the step of initiating the periodically applied transcranial magnetic stimulation at a predetermined sleep level.

18. The method of claim 17 further including ceasing the transcranial magnetic stimulation after a predetermined interval to be renewed at a renewed onset of the sleep level.

19. The method of claim 18 including the step of periodically ceasing the transcranial magnetic stimulation.

20. The method of claim 17 wherein the sleep level is characterized by onset of a predetermined amount of slow-wave activity.

21. The method of claim 16 wherein the transcranial magnetic stimulation is applied at the resting person's sensory-motor/parietal cortex near a midline of the brain.

22. An apparatus for assessing consciousness of an individual comprising:

a brain stimulator for applying external transcranial magnetic stimulation of the brain of the individual to evoke slow wave activity;

an EEG monitor monitoring slow wave activity of the brain of the individual after the periodic stimulation to measure a state of consciousness as a function of an effect of the application of transcranial magnetic stimulation by the brain stimulator on such slow wave activity and an output providing a quantitative measure of consciousness state to a healthcare worker.

* * * * *